United States Patent [19]

Saeki et al.

[11] Patent Number: 4,942,229
[45] Date of Patent: Jul. 17, 1990

[54] PROCESS FOR THE PRODUCTION OF PENICILLANIC ACID COMPOUNDS

[75] Inventors: Kazumi Saeki; Masami Hirano; Kunihide Oka; Kazuto Tsukinuki; Setsuo Oikawa, all of Nakatsu, Japan

[73] Assignee: Yoshitomi Pharmaceutical Industries, Ltd., Osaka, Japan

[21] Appl. No.: 310,595

[22] Filed: Feb. 13, 1989

[51] Int. Cl.$^5$ ............................................. C07D 499/08
[52] U.S. Cl. .................................... 540/310; 540/318; 540/339
[58] Field of Search ..................... 540/318, 310, 339; 514/196

[56] References Cited

U.S. PATENT DOCUMENTS

| | | | |
|---|---|---|---|
| 4,072,677 | 2/1978 | Callander | 540/318 |
| 4,234,579 | 11/1980 | Barth | 540/318 X |
| 4,244,951 | 1/1981 | Bigham | 540/310 X |
| 4,342,772 | 8/1982 | Godtfredsen et al. | 540/306 X |
| 4,381,263 | 4/1983 | Jasys | 540/318 X |
| 4,530,792 | 7/1985 | Weeks | 540/310 |
| 4,704,456 | 11/1987 | Adams | 540/310 |

FOREIGN PATENT DOCUMENTS 0645902 10/1984 Switzerland .
2137193 10/1984 United Kingdom .

OTHER PUBLICATIONS

"Chem. Abst.", 106(1), col. 4749f (1987).

Primary Examiner—Werren B. Lone
Assistant Examiner—Vera C. Clarke
Attorney, Agent, or Firm—Wenderoth, Lind & Ponack

[57] ABSTRACT

An improved process for the production of penicillic acid compounds, especially chloromethyl ester of penicillin G, penicillin V or sulbactam is disclosed.

10 Claims, No Drawings

PROCESS FOR THE PRODUCTION OF PENICILLANIC ACID COMPOUNDS

BACKGROUND OF THE INVENTION

1. Field of the Invention

This invention relates to an improved process for the production of penicillanic acid compounds which are useful as intermediates in the synthesis of penicillin series of antimicrobial agents.

2. Description of the Prior Art

Penicillanic acid 1,1-dioxide (sulbactam) is known as an useful β-lactamase inhibitor. A mutual prodrug derived from said sulbactam and ampicillin, namely 1,1-dioxopenicillanoyloxymethyl 6-[D-(2-amino-2-phenylacetylamino)]penicillanate (sultamicillin) is a drug developed for increasing the blood and tissue concentrations of ampicillin and sulbactam and for attaining synergism therebetween in β-lactamase resistance. Japanese Kokai Tokkyo Koho JP No. 59-98090 or U.S. Pat. No. 4,530,792 discloses 1,1-dioxopenicillanoyloxymethyl 6-(2-phenyl or phenoxy-acetylamino)penicillanate (hereinafter referred to as "compound A") and a method of producing sultamicillin from said compound A. The method disclosed for producing compound A comprises either reacting a salt of 6-(2-phenylacetylamino)penicillanic acid (penicillin G) or 6-(2-phenoxyacetylamino)penicillanic acid (penicillin V) with chloromethyl phenicillanate 1,1-dioxide (chloromethyl ester of sulbactam) or reacting a salt of sulbactam with chloromethyl 6-(2-phenylacetylamino)penicillanate (chloromethyl ester of penicillin G) or chloromethyl 6-(2-phenoxyacetylamino)penicillanate (chloromethyl ester of penicillin V). Such chloromethyl ester compounds are particularly important intermediates in the synthesis of diester compounds.

A number of references may be cited concerning the production of such chloromethyl ester compounds. Thus, for instance, Swiss Patent No. 645,902 discloses a method of chloromethyl esterification which comprises reacting sulbactam with chloroiodomethane in an appropriate solvent. Further, the above U.S. Pat. No. 4,530,792 or Japanese Kokai Tokkyo Koho JP No. 59-98090 discloses a method of producing such chloromethyl ester compounds which comprises reacting sulbactam, penicillin G or penicillin V with tetrabutylammonium hydroxide and then reacting the resulting tetramethylammonium salt with chloroiodomethane.

The above-mentioned known reactions for producing said chloromethyl ester compounds generally give low yields and require column separation for purification, hence are not fully satisfactory from the industrial viewpoint. Furthermore, the chloromethylating agent used there, namely chloroiodomethane, is a very expensive. It is difficult to obtain said compound commercially at low cost. A process is also known which comprises, for increasing the reactivity of sulbactam, penicillin G or penicillin V, reacting the same with a sufficient amount of tetrabutylammonium hydroxide, tetrabutylammonium chloride or the like to convert the same to the corresponding tetrabutylammonium salt and then reacting said salt with an excessive amount of chloroiodomethane under anhydrous conditions. However, this process has various problems: for instance, it involves two reaction steps, the operation is troublesome, the yield is low and, as for the reaction period, it is sometimes necessary to carry out the reaction overnight with stirring.

Further U.S. Pat. No. 4,704,456 discloses that a process for the preparation of chloromethyl ester of sulbactam which comprises reacting the tetrabutylammonium salt of sulbactam with a molar excess of bromochloromethane or chloroiodomethane in a solvent comprising said molar excess of bromochloromethane or chloroiodomethane in the presence of 0.1 to 1.0 molar equivalents of a beta-diketone or a tertiary amine. The process is troublesome from the industrial viewpoint since the tetrabutylammonium salt of sulbactam has to be isolated and reacted with bromochloromethane or chloroiodomethane in the dark.

DISCLOSURE OF THE INVENTION

This invention provides an improved process for the production of the chloromethyl ester of penicillin G, penicillin V or sulbactam as represented by the general formula

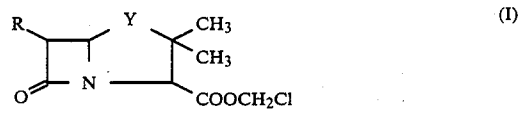

wherein R is hydrogen, phenylacetylamino or phenoxyacetylamino and Y is sulfur or sulfonyl, and have now complete the present invention.

Thus the present ivnention is concerned with a process for the production of penicillanic acid compounds of general formula (I) which comprises reacting a compound of the general formula

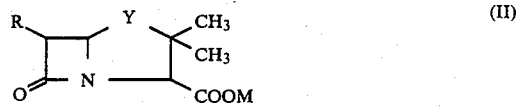

wherein R is hydrogen, phenylacetylamino or phenoxyacetylamino and Y is sulfur or sulfonyl and M is hydrogen or an alkali metal, with bromochloromethane in the presence of a phase transfer catalyst of the general formula

wherein $R^1$, $R^2$, $R^3$ and $R^4$ are the same or different and each is an alkyl or aralkyl group and X is a hydroxide, chloride, bromide or hydrogensulfate ion.

The staring material of this invention may be any of the compounds represented by general formula (II), provided that it is soluble in water. The sodium salt, potassium salt and the like are preferred, however.

On the other hand, for smooth progress of the reaction, bromochloromethane is used in excess, preferably in an amount of scores to hundreds of moles per mole of the compound of general formula (II).

Referring to the compound of general formula (III), which is used as a phase transfer catalyst, the alkyl group is, for example, methyl, ethyl, propyl, isopropyl, butyl, isobutyl, tert-butyl, pentyl, hexyl, heptyl, octyl, nonyl or decyl, while the aralkyl group is, for example, benzyl, phenylethyl or phenylpropyl. As typical examples of said compound, there may be mentioned tetramethylammonium chloride, benzyltrimethylammonium chloride, benzyltriethylammonium chloride, benzyltributylammonium chloride, tetrabutylammonium bromide, tetrabutylammonium hydrogen sulfate, tetrabutylammonium chloride, tetrabutylammonium hydroxide and trioctylammonium chloride, among others. Said compound is used in an amount equimolar or less in relation to the starting compound of general formula (II).

Smooth progress of the reaction can be secured by maintaining, during the reaction period, the solution in a weakly alkaline state with potassium hydrogen carbonate, sodium hydrogen carbonate or the like substance. Such substance is used in an amount of about 0.1 mole per of the starting compound of general formula (II).

Surprisingly, the reaction can be carried out at a temperature within the range from room temperature to 60° C., preferably at 30°–50° C. with heating. The reaction period required may vary depending on the amount of the phase transfer catalyst, the reaction temperature and other factors. Generally, however, the reaction may be carried out for 1–12 hours.

The chloromethyl ester compound thus obtained is contained in the bromochloromethane layer separated after reaction from the aqueous layer and can be obtained as a residue after removal of the excess bromochloromethane by distillation. The chloromethyl ester compound obtained has a high purity and can be submitted as such to the next esterification step, namely the production of compound A, without purification. Furthermore, the bromochloromethane reconverged can be recycled without purification.

Thus the process according to the invention is advantageous from the yield, purity and reaction procedure viewpoints as compared with the prior art processes. For instance, (1) the desired products can be obtained in high yields and high purities; (2) the use of bromochloromethane as the chloromethylating agent renders it unnecessary to maintain a low reaction temperature but, to the contrary makes it possible to carry out the reaction within the temperature range of from room temperature to 60° C. (with heating), resulting in reduction of the byproduct bis ester to a level of 10% or below and at the same time in reduction of the reaction period; (3) bromochloromethane is quite inexpensive as compared with chloroiodomethane, hence is advantageous from the industrial viewpoint; and (4) the presence of the phase transfer catalyst makes it possible to produce the desired products in one reaction step while the reaction mixture is maintained in an emulsion state; the products are high in purity and can be submitted to the subsequent reaction without further purification and therefore the procedure can be much simplified. In this way, the compound A, which is useful as an intermediate in the synthesis of antibiotics, in particular sultamicillin, can be produced with good efficiency and in an advantageous manner.

[EXAMPLES]

The following examples illustrate the invention in further detail but are by no means limitative of the scope of the invention. The compounds obtained were identified by such means as IR spectrometry, NMR spectrometry, HPLC and elemental analysis.

Example 1:

Chloromethyl 6-(2-phenylacetylamino)penicillanate

A mixture of 300 g of bromochloromethane, 10 g of water and 1.3 g of 50.9% tetrabutylammonium bromide was maintained at 45° C., and a solution composed of 7.45 g of potassium 6-(2-phenylacetylamino)penicillanate, 40 g of water and 0.2 g of potassium bicarbonate was poured into said mixture. The reaction was carried out at 45° C. with vigorous stirring for 8 hours. When the reaction was completed, the reaction mixture contained potassium 6-(2-phenylacetylamino)penicillanate, chloromethyl 6-(2-phenylacetylamino)penicillanate and methylene bis[6-(2-phenylacetylamino)penicillanate] in the ratio of 6.5 : 85.6 : 7.9 (HPLC area ratio). The reaction mixture was cooled, and the organic layer was separated, washed with water and concentrated under reduced pressure to give 7.4 g of a light brown oil. This oil had the following composition: potassium 6-(2-phenylacetylamino)penicillanate : chloromethyl 6-(2-phenylacetylamino)penicillanate : methylene bis[6-(2-phenylacetylamino)penicillanate]=0.23 : 85.63 : 9.78 (HPLC area ratio).

Example 2:

Chloromethyl penicillanate 1,1-dioxide

A solution composed of 2.55 g of sodium penicillanate 1,1-dioxide, 20 g of water and 0.08 g of sodium hydrogen carbonate was poured into a mixture, maintained at 40° C., of 300 g of bromochloromethane, 5 g of water and 0.65 g of 50.9% tetrabutylammonium bromide. The reaction was carried out at 40° C. with vigorous stirring for 12 hours. The organic layer was separated and washed with water and, then, the bromochloromethane was distilled off. The residue had the composition: chloromethyl penicillanate 1,1-dioxide : methylene bis[1,1-dioxopenicillanate]=94.6 : 5.4 (HPLC area ratio). Part of the residue was allowed to stand in a refrigerator, whereupon crystals formed. The crystals were collected by filtration and washed with a small amount of a mixed solvent composed of ether and petroleum ether to give the desired product having a melting point of 94°–96° C. in a crystalline form. The IR spectrum of this product was in complete agreement with that of an authentic sample [synthesized by the method described by B. Baltzer et al. in Journal of Antibiotics, vol. 33, page 1183 (1980)].

What is claimed is:

1. A process for the production of a penicillanic acid compound of the formula

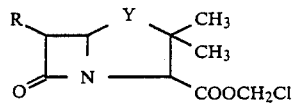

wherein R is hydrogen, phenylacetylamino or phenoxyacetylamino and Y is sulfur or sulfonyl, which comprises reacting a compound of the formula

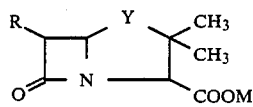

wherein R and Y are as defined above and M is hydrogen or an alkali metal, with bromochloromethane in the presence of a phase transfer catalyst of the formula

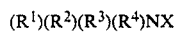

wherein $R^1$, $R^2$, $R^3$ and $R^4$ are the same or different and each is an alkyl or aralkyl group and X is a hydroxide, chloride, bromide or hydrogensulfate ion.

2. The process according to claim 1, wherein the reaction is carried out at a temperature between 30° C. and 60° C.

3. The process according to claim 1, wherein R is phenylacetylamino or phenoxyacetylamino and Y is sulfur.

4. The process according to claim 1, wherein R is hydrogen and Y is sulfonyl.

5. The process according to claim 1, wherein the reaction is carried out in the presence of excess bromochloromethane and water.

6. The process according to claim 1, wherein the reaction is carried out using tetrabutylammonium bromide in an amount equimolar or less to the compound of the formula

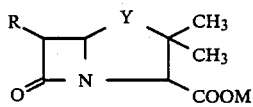

wherein R is hydrogen, phenylacetylamino or phenoxyacetylamino, Y is sulfur or sulfonyl and M is hydrogen or an alkali metal, and excess bromochloromethane.

7. The process according to claim 1, wherein the reaction is carried out using 0.1 molar quantity of tetrabutylammonium bromide and excess bromochloromethane.

8. The process according to claim 1, wherein the reaction is carried out in the presence of 0.1 molar quantity or more of $KHCO_3$ or $NaHCO_3$ to the compound of the formula

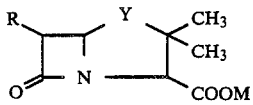

wherein R is hydrogen, phenylacetylamino or phenoxyacetylamino, Y is sulfur or sulfonyl and M is hydrogen or an alkali metal.

9. The process according to claim 1, wherein unreacted potassium 6-(2-phenylacetylamino)penicillanate and bromochloromethane recovered are used.

10. The process according to claim 1, wherein unreacted sodium penicillanate 1,1-dioxide and bromochloromethane recovered are used.

* * * * *